(12) United States Patent
Plattner et al.

(10) Patent No.: US 8,227,459 B2
(45) Date of Patent: Jul. 24, 2012

(54) DIAMINO-PHENOTHIAZINYL DERIVATIVES AS ANTIVIRAL TREATMENTS

(75) Inventors: Jacob Plattner, Berkeley, CA (US); Colm Kelleher, Lafayette, CA (US); Vishwanath Lingappa, San Francisco, CA (US); Beverly Freeman, Albany, CA (US); William Hansen, San Francisco, CA (US)

(73) Assignee: Prosetta Antiviral Inc., San Francisco, CA (US)

(*) Notice: Subject to any disclaimer, the term of this patent is extended or adjusted under 35 U.S.C. 154(b) by 1094 days.

(21) Appl. No.: 12/062,491

(22) Filed: Apr. 3, 2008

(65) Prior Publication Data

US 2011/0178071 A1 Jul. 21, 2011

Related U.S. Application Data

(60) Provisional application No. 60/909,928, filed on Apr. 3, 2007.

(51) Int. Cl.
*A61K 31/54* (2006.01)
(52) U.S. Cl. .................................... 514/224.8
(58) Field of Classification Search .......................... None
See application file for complete search history.

(56) References Cited

FOREIGN PATENT DOCUMENTS

| WO | WO 02/096896 | * | 12/2002 |
| WO | 2006/032879 A | | 3/2006 |
| WO | WO 2006/032847 | * | 3/2006 |

OTHER PUBLICATIONS

Wainwright, "Methylene blue derivatives—suitable photoantimicrobials for blood product disinfection?" Review Article, International Journal of Antimicrobial Agents 16 (2000) 381-394.*
Amaral et al. "Phenothiazines: potential management of Creutzfeldt-Jacob disease and its variants" Int. Journal of Antimicrobial Agents 18 (2001) 411-417.*
Papin, et al. "Methylene blue photoinactivation abolishes West Nile virus infectivity in vivo" Antiviral Research 68 (2): 84-87 Nov. 1, 2005.

* cited by examiner

*Primary Examiner* — Jeffrey S. Lundgren
*Assistant Examiner* — William Lee
(74) *Attorney, Agent, or Firm* — David P. Lentini

(57) ABSTRACT

Compounds and methods for preventing and treating viral infections are provided. In some embodiments, novel compounds broad-spectrum antiviral activity are provided. In more specific embodiments, the compounds and methods are effective against viruses such as Venezuelan Equine Encephalitis, West Nile Virus, and Hepatitis C.

27 Claims, 4 Drawing Sheets

Figure 1A

EBOV Control

Legend: ■ Dead ▨ Sick ▧ Ruffled ☐ Healthy

Figure 1B

EBOV Treated

Legend: ■ Dead, ▨ Sick, ▨ Ruffled, □ Healthy

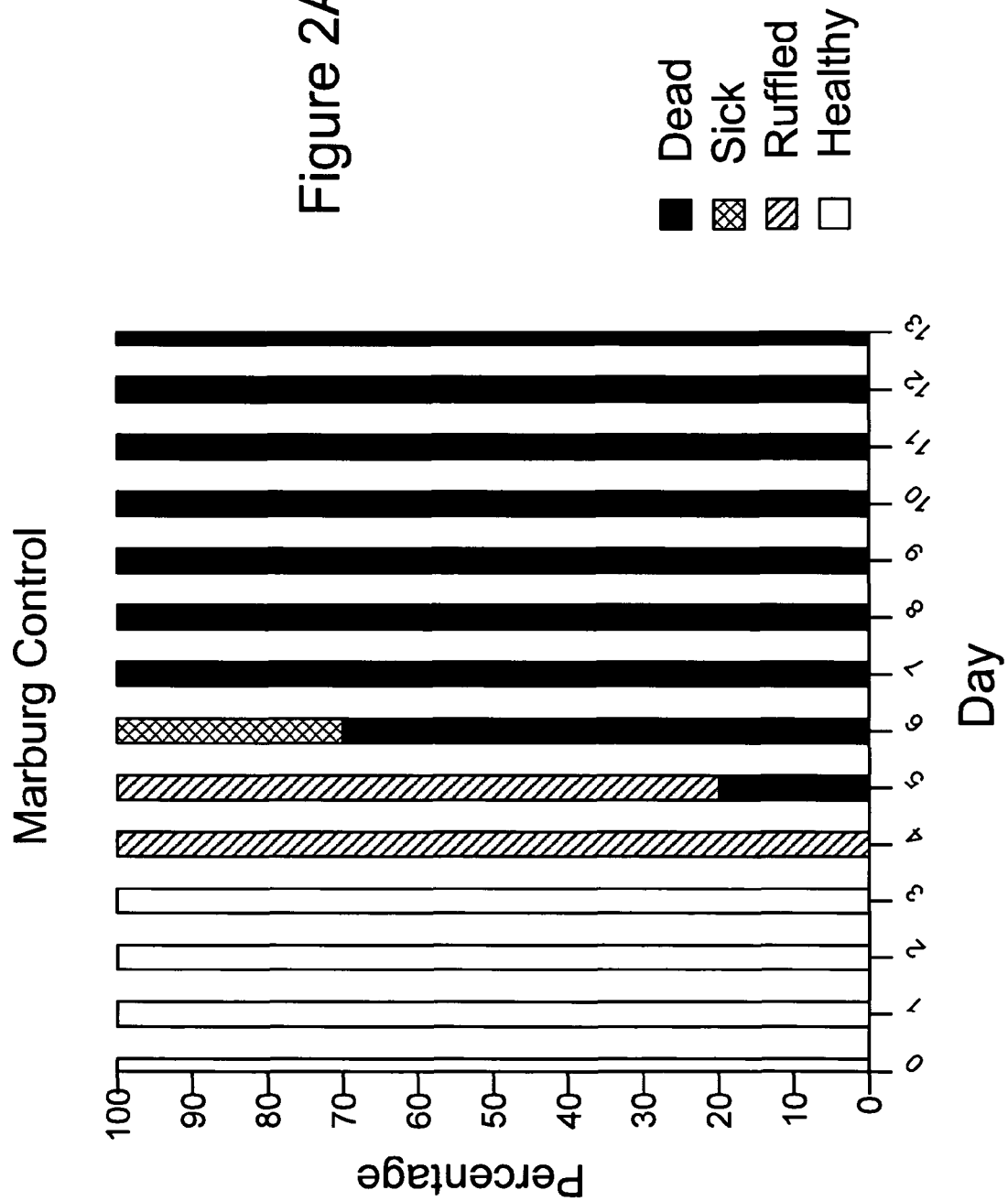

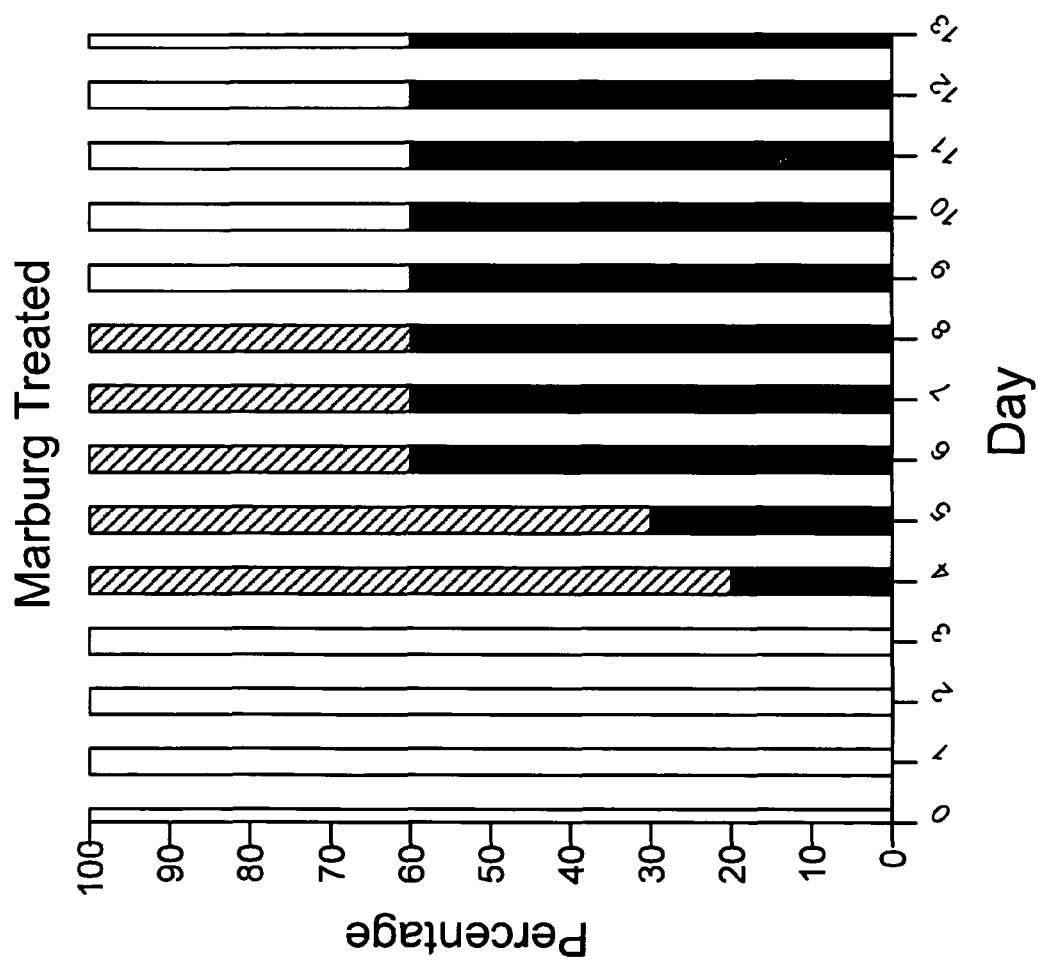

DIAMINO-PHENOTHIAZINYL DERIVATIVES AS ANTIVIRAL TREATMENTS

CROSS-REFERENCE TO RELATED APPLICATION

This application claims priority under 35 U.S.C. §119(e) to provisional U.S. Patent Application Ser. No. 60/909,928 filed 3 Apr. 2007, the entire disclosure of which in incorporated herein by reference in its entirety and for all purposes.

1 BACKGROUND OF THE INVENTION 1.1 Field of the Invention

The present invention provides compositions and methods for preventing and treating viral infections. The present invention thus has applications in the areas of medicine, pharmacology, virology, and medicinal chemistry.

1.2 The Related Art

Few good options are available for preventing or treating viral infections. The vast majority of antiviral drugs interfere with viral replication through the inhibition of transcription of the viral genome. Commonly these drugs inhibit a specific protein involved in viral genomic transcription, such as a polymerase or transcriptase; which often produces unwanted toxicity, since viruses depend largely on host factors for viral genomic replication. Moreover, given the highly specific nature of the target, small mutations in the viral genome are often sufficient to create viral strains that are resistant to chemotherapeutics. In addition, since the drugs inhibit active viral replication, they cannot eliminate virus that is latent or sequestered in the host; thus, patients are forced to take antivirals—and endure their toxic effects—for long periods if not indefinitely. Not surprisingly, patients on such regimens cannot continue treatment, and remain infected as well as providing a potentially continuing source of additional infections.

Thus there is a need for better antiviral chemotherapeutics and more effective strategies for identifying such chemotherapeutics. The need is especially urgent for those suffering from chronic and debilitating viral infections, such as human immunodeficiency virus (HIV) and hepatitis C(HCV), for which no good treatment exists for the reasons noted above.

But new viral threats are also on the horizon. The steady encroachment of civilization into the most remote regions of the globe has introduced the risk of exotic viral infections to the population at large. Each passing year brings an increasing number of reports of infections by hemorragic fevers, such as Ebola virus (EBOV), Marburg virus (Marburg), and Rift Valley Fever virus (RVFV). Still other viral infections can cause potentially debilitating effects, such as recurrent fevers, joint pain, and fatigue; these include: Punta Toro Virus (PTV), West Nile virus (WNV), chikungunya virus (CHK), Easter Equine Encephalitis virus (EEEV), Wester Equine Encephalitis virus (WEEV), Lhasa virus (LASV), and Dengue virus (DENY).

By way of example, one of the additional "new" viruses (that is, new with respect to the industrialized world) is Venezuelan Equine Encephalitis virus (also called Venezuelan equine encephalomyelitis, "VEEV"). VEEV is a mosquito-borne viral disease of all equine species, including horses, asses, (wild and domestic), and zebras. Equines infected with VEEV may show one or more of the following signs: fever, depression, loss of appetite weakness, and central nervous system disorders (lack of coordination, chewing movements, head pressing, "sawhorse" stance, circling, paddling motion of the limbs, and convulsions). In some cases, horses infected with VEEV may show no clinical signs before dying. The clinical signs of VEEV can be confused with those of other diseases that affect the central nervous system. These include eastern equine encephalitis, western equine encephalitis, African horse sickness, rabies, tetanus, and bacterial meningitis. VEE might also be mistaken for toxic poisoning. Definitive diagnosis can be made by isolating the virus in a laboratory or by testing blood for the presence of antibodies to the virus.

Humans also can contract this disease. Healthy adults who become infected by the virus may experience flu-like symptoms, such as high fevers and aches; and those having weakened immune systems, as well as the young and elderly, can become more severely ill or even die.

The virus that causes VEEV is transmitted primarily by mosquitoes that bite an infected animal and then bite and feed on another animal or human. The speed with which the disease spreads depends on the subtype of the VEEV virus and the density of mosquito populations. Enzootic subtypes of VEEV are diseases endemic to certain areas. Generally these serotypes do not spread to other localities. Enzootic subtypes are associated with the rodent-mosquito transmission cycle. These forms of the virus can cause human illness but generally do not affect equine health. Epizootic subtypes, on the other hand, can spread rapidly through large populations. These forms of the virus are highly pathogenic to equines and can also affect human health. Equines, rather than rodents, are the primary animal species that carry and spread the disease. Infected equines develop an enormous quantity of virus in their circulatory system. When a blood-feeding insect feeds on such animals, it picks up this virus and transmits it to other animals or humans. Although other animals, such as cattle, swine, and dogs, can become infected, they generally do not show signs of the disease or contribute to its spread.

Naturally occurring outbreaks of VEEV are rare. In 1936, VEEV was first recognized as a disease of concern in Venezuela following a major outbreak of equine encephalomyelitis. From 1936 to 1968, equines in several South American countries suffered devastating outbreaks. In 1969, the disease moved north throughout Central America, finally reaching Mexico and Texas in 1971. The highly pathogenic form of VEEV has not occurred in the United States since 1971. However, in 1993 an outbreak of VEEV in the State of Chiapas, Mexico, prompted the U.S. Department of Agriculture to temporarily increase its surveillance activities and tighten its quarantine requirements for equine species entering the United States from Mexico. During outbreaks, the most effective way to prevent further spread of disease is to quarantine infected equines. Controlling mosquito populations through pesticide treatments and eliminating insect-breeding sites will also enhance disease control. These measures should be accompanied by a large-scale equine immunization program. Equines in the United States should be vaccinated for VEE only when there is a serious threat that the disease could spread to this country.

Similar to VEE is West Nile virus ("WNV"), which was mentioned above. West Nile virus is named for a district in Uganda where the virus was first identified in humans in 1937. Outbreaks of the virus have occurred in a number of countries throughout Europe, the Middle East, Africa, Central Asia, and Australia, since that time. WNV was first detected in the Western Hemisphere in 1999, and since then the disease has spread across North America, Mexico, Puerto Rico, the Dominican Republic, Jamaica, Guadeloupe, and El Salvador. Symptoms range from a mild, flulike illness (fever, headache, muscle and joint pain) and a red, bumpy rash, to meningitis. In rare cases those infected will develop encephalitis, which can include high fever, a stiff neck, disorientation, paralysis, convulsions, coma, and death in about 10 percent of cases.

No cure or treatment is available for either VEEV or WNV, or the other viruses listed above; so public health experts emphasize prevention by avoiding areas where the disease has been detected or where disease vectors (usually mosquitos) have been identified. However, that approach is becoming less reasonable as the world population grows. Moreover, some officials fear that one or both of these diseases, or other similar viruses in the toga- and flaviviridae, could be "weaponized" by a hostile government or terrorist organization to immobilize military personnel or important segments of the population in an attack.

To make matters still more complicated, the above-mentioned viral threats span almost all of the recognized viral families, including the bunyaviruses, flaviviruses, filoviruses, arenaviruses, and togaviruses. Since viral families are defined in significant part by their differences in mechanism for genomic replication, therapeutic strategies that are focused on inhibiting genomic replication will be inadequate for large outbreaks of new, and especially weaponized, viruses.

Thus, there is an acute need to provide medicinal treatments for these and other viral diseases. The present invention meets these and other needs.

2 SUMMARY OF THE INVENTION

The present invention provides novel anti-viral compounds and methods for preventing and treating viral infections. Surprisingly, the compounds and methods provided by the invention are active against a broad range of virus families; and the compounds and methods of the invention have activity as broad-spectrum anti-viral therapies.

In a first aspect, the present invention provides a compound having the structure:

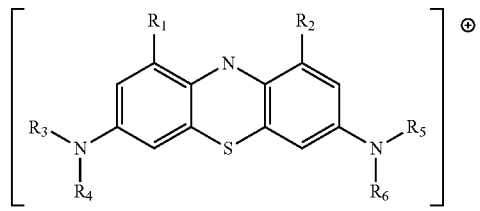

including the pharmaceutically acceptable salts, solvates, and hydrates thereof. $R_1$ and $R_2$ are selected independently from the group consisting of: hydrogen, halo, cyano, carbonyl, carboxyl, and optionally substituted lower alkyl, optionally substituted lower alkyloxy, and optionally substituted lower alkylcarbonyl. $R_3$-$R_6$ are selected independently from the group consisting of: optionally substituted lower alkyl and lower hydroxyalkyl, and further $R_3$ and $R_4$, and $R_5$ and $R_6$, together with the nitrogens to which they are attached respectively, may form independently an optionally substituted saturated or unsaturated five- or six-membered ring. However, none of $R_3$-$R_6$ is substituted or unsubstituted $C_{1-4}$ alkyl, substituted or unsubstituted $C_{2-4}$ alkenyl when both $R_1$ and $R_2$ are selected from the group consisting of hydrogen, $C_{1-4}$ alkyl, $C_{2-4}$ alkenyl, or halogenated $C_{1-4}$ alkyl; and none of $R_3$-$R_6$, together with the nitrogens to which they are attached respectively, forms piperazin-1-yl when both $R_1$ and $R_2$ are hydrogen.

In some embodiments of at least one of $R_1$ and $R_2$ is hydrogen, and, in more specific embodiments of the foregoing, both $R_1$ and $R_2$ are hydrogen. In other embodiments, at least one of $R_3$-$R_6$' together with the nitrogens to which they are attached respectively, is an optionally substituted saturated or unsaturated five- or six-membered ring; in more specific embodiments of the foregoing, the aforementioned five- or six-membered ring is saturated. Still more specific embodiments are those in which the aforementioned saturated five- or six-membered ring is a five-membered ring. In yet more specific embodiments, the aforementioned saturated five-membered ring is pyrrolyl.

In another aspect, the invention provides the novel compounds shown below and their pharmaceutically acceptable salts, hydrates, and complexes:

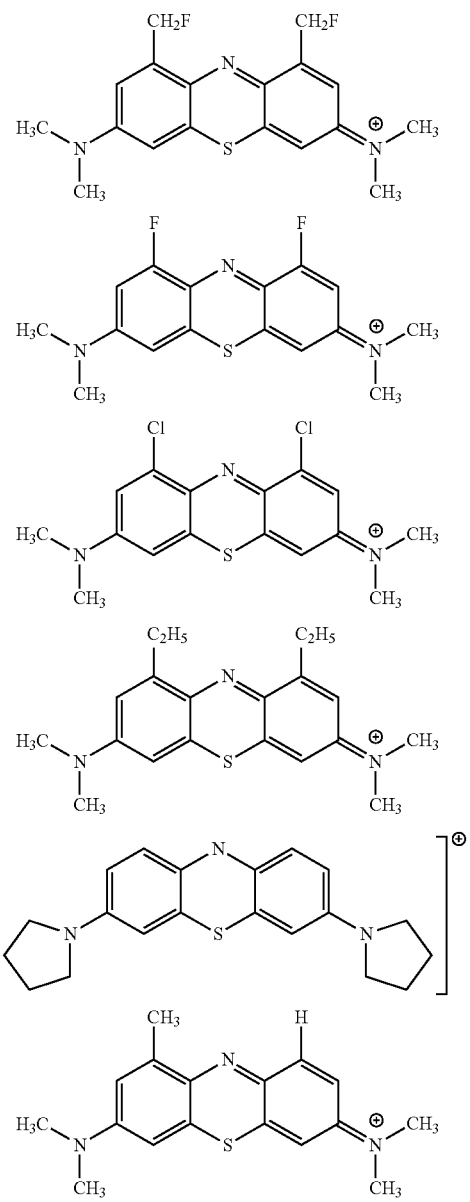

In yet another aspect, the present invention provides a method for treating an animal infected with a virus, comprising administering to such animal a therapeutically effective amount of a compound having the structure:

$$\left[\begin{array}{c}R_1 \quad\quad R_2 \\ \text{(phenothiazine core with N at top, S at bottom,} \\ R_3R_4N\text{— on left ring, —}NR_5R_6 \text{ on right ring)}\end{array}\right]^{\oplus}$$

including the pharmaceutically acceptable salts, solvates, and hydrates thereof. $R_1$ and $R_2$ are selected independently from the group consisting of: hydrogen, halogen, cyano, carbonyl, carboxyl, and optionally substituted lower alkyl, optionally substituted lower alkyloxy, and optionally substituted lower alkylcarbonyl. $R_3$-$R_6$ are selected independently from the group consisting of: optionally substituted lower alkyl and lower hydroxyalkyl, and further $R_3$ and $R_4$, and $R_5$ and $R_6$, together with the nitrogens to which they are attached respectively, may form independently an optionally substituted saturated or unsaturated five- or six-membered ring.

In some embodiments, the virus is selected from the group consisting of: HCV, VEEV, RVFV, LASV, and EBOV.

These elements and other aspects and advantages of the invention will be apparent when the following Description is read in conjunction with the accompanying Drawings.

3 BRIEF DESCRIPTION OF THE DRAWING

Figure 1A:
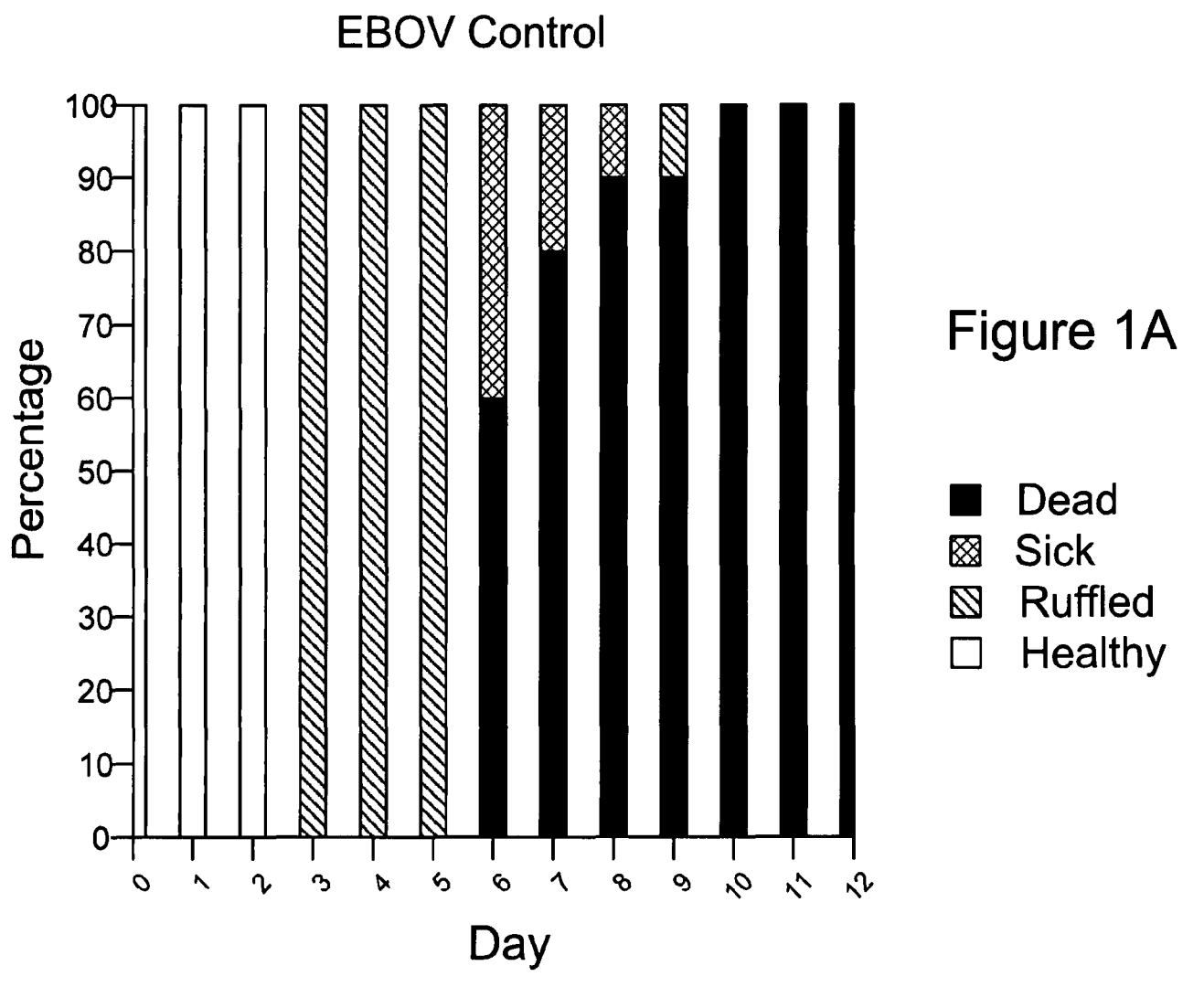
Figure 1B:
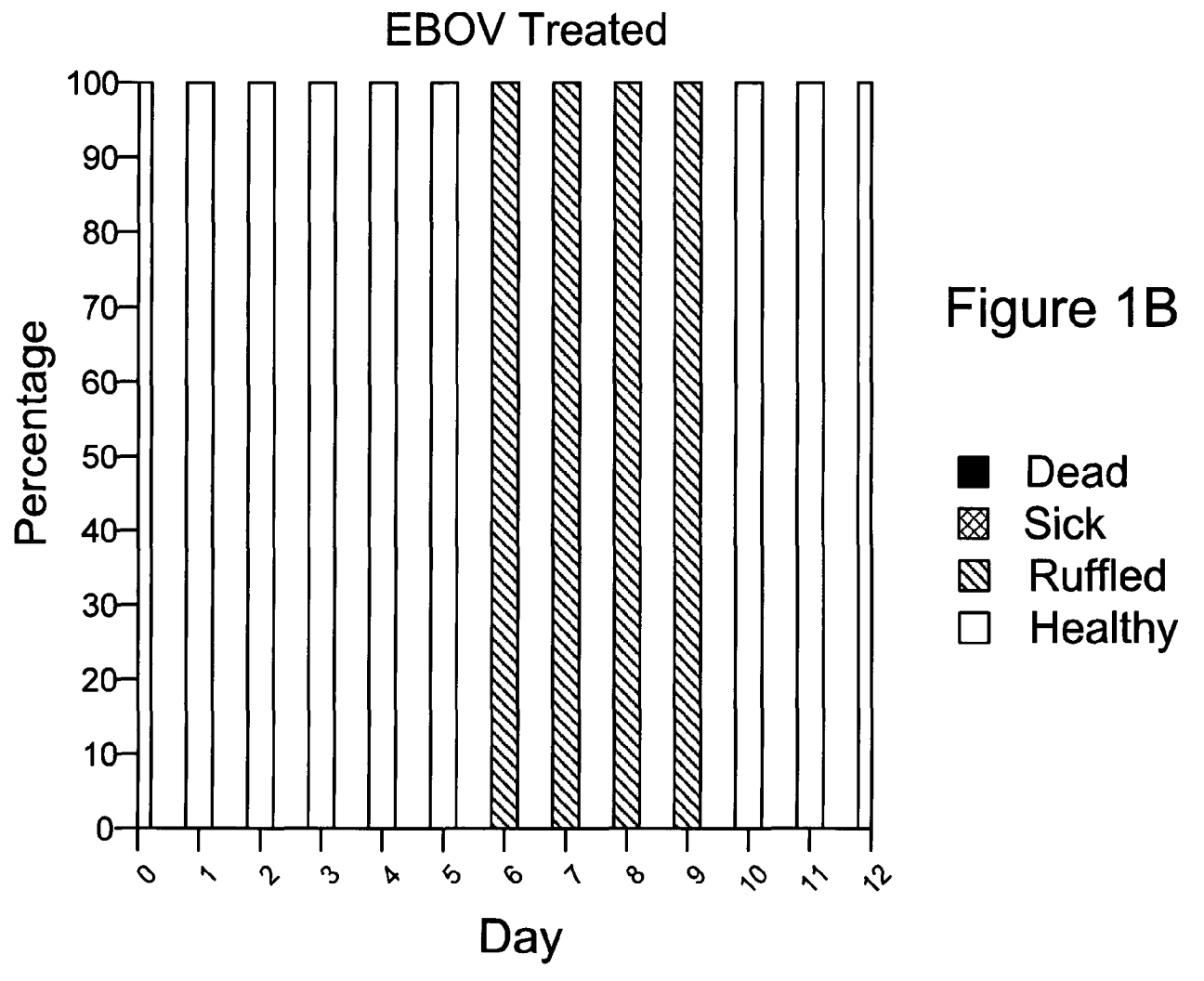

FIGS. 1A and 1B illustrate a study in which a compound of the invention was tested for its ability to protect mice from Ebola (EBOV) infection. FIG. 1A shows the results for the control group. FIG. 1B shows the results for the study group.

FIGS. 2A and 2B illustrate a study in which a compound of the invention was tested for its ability to protect mice from Marburg virus infection. FIG. 2A shows the results for the control group. FIG. 2B shows the results for the study group.

4 DESCRIPTION OF SOME EMBODIMENTS OF THE INVENTION

4.1 Definitions
4.1.1 Optionally Substituted

"Optionally substituted" refers to the replacement of hydrogen with a monovalent or divalent radical. Suitable substitution groups include, for example, hydroxyl, nitro, amino, imino, cyano, halo, thio, thioamido, amidino, oxo, oxamidino, methoxamidino, imidino, guanidino, sulfonamido, carboxyl, formyl, loweralkyl, haloloweralkyl, loweralkoxy, haloloweralkoxy, loweralkoxyalkyl, alkylcarbonyl, arylcarbonyl, aralkylcarbonyl, heteroarylcarbonyl, heteroaralkylcarbonyl, alkylthio, aminoalkyl, cyanoalkyl, and the like. The substitution group can itself be substituted. The group substituted onto the substitution group can be, for example, carboxyl, halo; nitro, amino, cyano, hydroxyl, loweralkyl, loweralkoxy, aminocarbonyl, —SR, thioamido, —SO$_3$H, —SO$_2$R or cycloalkyl, where R is typically hydrogen, hydroxyl or loweralkyl. When the substituted substituent includes a straight chain group, the substitution can occur either within the chain (e.g., 2-hydroxypropyl, 2-aminobutyl, and the like) or at the chain terminus (e.g. 2-hydroxyethyl, 3-cyanopropyl, and the like). Substituted substitutents can be straight chain, branched or cyclic arrangements of covalently bonded carbon or heteroatoms.

4.1.2 Loweralkyl and Related Terms

"Loweralkyl" as used herein refers to branched or straight chain alkyl groups comprising one to ten carbon atoms that independently are unsubstituted or substituted, e.g., with one or more halogen, hydroxyl or other groups. Examples of loweralkyl groups include, but are not limited to, methyl, ethyl, propyl, isopropyl, n-butyl, t-butyl, n-hexyl, neopentyl, trifluoromethyl, pentafluoroethyl, and the like.

"Alkyl" refers to a divalent straight chain or branched chain saturated aliphatic radical having from 1- to 20 carbon atoms. Typical alkyl groups employed in compounds of the present invention are loweralkylenyl groups that have from 1 to about 6 carbon atoms in their backbone. "Alkenyl" refers herein to straight chain, branched, or cyclic radicals having one or more double bonds and from 2- to 20 carbon atoms. "Alkynyl" refers herein to straight chain, branched, or cyclic radicals having one or more triple bonds and from 2- to 20 carbon atoms.

The term "haloloweralkyl" refers to a loweralkyl radical substituted with one or more halogen atoms.

"Loweralkoxy" as used herein refers to RO— wherein R is loweralkyl. Representative examples of loweralkoxy groups include methoxy, ethoxy, t-butoxy, trifluoromethoxy and the like.

"Loweralkylhio" as used herein refers to RS— wherein R is loweralkyl.

The term "alkoxyalkyl" refers to the group -alk$_1$-O-alk$_2$ where alk$_1$ is alkylenyl or alkenyl, and alk$_2$ is alkyl or alkenyl. The term "loweralkoxyalkyl" refers to an alkoxyalkyl where alk$_1$ is loweralkylenyl or loweralkenyl, and alk$_2$ is loweralkyl or loweralkenyl. The term "aryloxyalkyl" refers to the group -alkylenyl-O-aryl. The term "aralkoxyalkyl" refers to the group -alkylenyl-O-aralkyl, where aralkyl is a loweralkyl.

"Cycloalkyl" refers to a mono- or polycyclic, loweralkyl substituent. Typical cycloalkyl substituents have from 3- to 8 backbone (i.e., ring) atoms in which each backbone atom is optionally substituted carbon. When used in context with cycloalkyl substituents, the term "polycyclic" refers herein to fused, non-fused cyclic carbon structures and spirocycles. Examples of cycloalkyl groups include, but are not limited to, cyclopropyl, cyclobutyl, cyclopentyl, cyclohexyl, adamantyl, bornyl, norbornyl, and the like.

The term "cycloheteroalkyl" refers herein to cycloalkyl substituents that have from 1 to 5, and more typically from 1 to 4 heteroatoms (i.e., non-carbon atoms such as nitrogen, sulfur, and oxygen) in the ring structure, with the balance of atoms in the ring being optionally substituted carbon. Representative heterocycloalkyl moieties include, for example, morpholino, piperazinyl, piperidinyl, pyrrolidinyl, methylpryolidinyl, pyrrolidinone-yl, and the like.

The terms "(cycloalkyl)alkyl" and "(cycloheteroalkyl)alkyl" refer to alkyl chains substituted with cycloalkyl and cycloheteroalkyl groups respectively.

The term "haloalkoxy" refers to an alkoxy radical substituted with one or more halogen atoms. The term "haloloweralkoxy" refers to a loweralkoxy radical substituted with one or more halogen atoms.

4.1.3 Halo

"Halo" refers herein to a halogen radical, such as fluorine, chlorine, bromine, or iodine.

4.1.4 Aryl and Related Terms

"Aryl" refers to monocyclic and polycyclic aromatic groups, or fused ring systems having at least one aromatic ring, having from 3- to 14 backbone carbon atoms. Examples of aryl groups include without limitation phenyl, naphthyl, dihydronaphtyl, tetrahydronaphthyl, and the like.

"Aralkyl" refers to an alkyl group substituted with an aryl group. Typically, aralkyl groups employed in compounds of the present invention have from 1- to 6 carbon atoms incorporated within the alkyl portion of the aralkyl group. Suitable aralkyl groups employed in compounds of the present invention include, for example, benzyl, picolyl, and the like.

4.1.5 Heteroaryl and Related Terms

The term "heteroaryl" refers herein to aryl groups having from one to four heteroatoms as ring atoms in an aromatic ring with the remainder of the ring atoms being aromatic or non-aromatic carbon atoms. When used in connection with aryl substituents, the term "polycyclic" refers herein to fused and non-fused cyclic structures in which at least one cyclic structure is aromatic, such as, for example, benzodioxozolo, naphthyl, and the like. Exemplary heteroaryl moieties employed as substituents in compounds of the present invention include pyridyl, pyrimidinyl, thiazolyl, indolyl, imidazolyl, oxadiazolyl, tetrazolyl, pyrazinyl, triazolyl, thiophenyl, furanyl, quinolinyl, purinyl, benzothiazolyl, benzopyridyl, and benzimidazolyl, and the like.

4.1.6 Amino and Related Terms

"Amino" refers herein to the group —$NH_2$. The term "loweralkylamino" refers herein to the group —NRR' where R and R' are each independently selected from hydrogen or loweralkyl. The term "arylamino" refers herein to the group —NRR' where R is aryl and R' is hydrogen, loweralkyl, aryl, or aralkyl. The term "aralkylamino" refers herein to the group —NRR' where R is aralkyl and R' is hydrogen, loweralkyl, aryl, or aralkyl. The terms "heteroarylamino" and heteroaralkylamino" are defined by analogy to arylamino and aralkylamino.

The term "aminocarbonyl" refers herein to the group —C(O)—$NH_2$. The terms "loweralkylaminocarbonyl", "arylaminocarbonyl", "aralkylaminocarbonyl", "heteroarylaminocarbonyl", and "heteroaralkylaminocarbonyl" refer to —C(O)NRR' where R and R' independently are hydrogen and optionally substituted loweralkyl, aryl, aralkyl, heteroaryl, and heteroaralkyl respectively by analogy to the corresponding terms above.

4.1.7 Thio, Sulfonyl, Sulfinyl and Related Terms

The term "thio" refers to —SH. The terms "loweralkylthio", "arylthio", "heteroarylthio", "cycloalkylthio", "cycloheteroalkylthio", "aralkylthio", "heteroaralkylthio", "(cycloalkyl)alkylthio", and "(cycloheteroalkyl)alkylthio" refer to —SR, where R is optionally substituted loweralkyl, aryl, heteroaryl, cycloalkyl, cycloheteroalkyl, aralkyl, heteroaralkyl, (cycloalkyl)alkyl, and (cycloheteroalkyl)alkyl respectively.

The term "sulfonyl" refers herein to the group —$SO_2$—. The terms "loweralkylsulfonyl", "arylsulfonyl", "heteroarylsulfonyl", "cycloalkylsulfonyl", "cycloheteroalkylsulfonyl", "aralkylsulfonyl", "heteroaralkylsulfonyl", "(cycloalkyl)alkylsulfonyl", and "(cycloheteroalkyl)alkylsulfonyl" refer to —$SO_2$R where R is optionally substituted loweralkyl, aryl, heteroaryl, cycloalkyl, cycloheteroalkyl, aralkyl, heteroaralkyl, (cycloalkyl)alkyl, and (cycloheteroalkyl)alkyl respectively.

The term "sulfinyl" refers herein to the group —SO—. The terms "loweralkylsulfinyl", "arylsulfinyl", "heteroarylsulfinyl", "cycloalkylsulfinyl", "cycloheteroalkylsulfinyl", "aralkylsulfinyl", "heteroaralkylsulfinyl", "(cycloalkyl)alkylsulfinyl, and "(cycloheteroalkyl)alkylsulfinyl" refer to —SOR where R is optionally substituted loweralkyl, aryl, heteroaryl, cycloalkyl, cycloheteroalkyl, aralkyl, heteroaralkyl, (cycloalkyl)alkyl, and (cycloheteroalkyl)alkyl respectively.

4.1.8 Formyl, Carboxyl, Carbonyl, Thiocarbonyl, and Related Terms

"Formyl" refers to —C(O)H.

"Carboxyl" refers to —C(O)OH.

"Carbonyl" refers to the divalent group —C(O)—. The terms "loweralkylcarbonyl", "arylcarbonyl", "heteroarylcarbonyl", "cycloalkylcarbonyl", "cycloheteroalkylcarbonyl", "aralkycarbonyl", "heteroaralkylcarbonyl", "(cycloalkyl)alkylcarbonyl", and "(cycloheteroalkyl)alkylcarbonyl" refer to —C(O)R, where R is optionally substituted loweralkyl, aryl, heteroaryl, cycloalkyl, cycloheteroalkyl, aralkyl, heteroaralkyl, (cycloalkyl)alkyl, and (cycloheteroalkyl)alkyl respectively.

"Thiocarbonyl" refers to the group —C(S)—. The terms "loweralkylthiocarbonyl", "arylthiocarbonyl", "heteroarylthiocarbonyl", "cycloalkylthiocarbonyl", "cycloheteroalkylthiocarbonyl", "aralkylhiocarbonyloxlthiocarbonyl", "heteroaralkylthiocarbonyl", "(cycloalkyl)alkylthiocarbonyl", and "(cycloheteroalkyl)alkylthiocarbonyl" refer to —C(S)R, where R is optionally substituted loweralkyl, aryl, heteroaryl, cycloalkyl, cycloheteroalkyl, aralkyl, heteroaralkyl, (cycloalkyl)alkyl, and (cycloheteroalkyl)alkyl respectively.

"Carbonyloxy" refers generally to the group —C(O)—O—. The terms "loweralkylcarbonyloxy", "arylcarbonyloxy", "heteroarylcarbonyloxy", "cycloalkylcarbonyloxy", "cycloheteroalkylcarbonyloxy", "aralkycarbonyloxy", "heteroaralkylcarbonyloxy", "(cycloalkyl)alkylcarbonyloxy", "(cycloheteroalkyl)alkylcarbonyloxy" refer to —C(O)OR, where R is optionally substituted loweralkyl, aryl, heteroaryl, cycloalkyl, cycloheteroalkyl, aralkyl, heteroaralkyl, (cycloalkyl)alkyl, and (cycloheteroalkyl)alkyl respectively.

"Oxycarbonyl" refers to the group —O—C(O)—. The terms "loweralkyloxycarbonyl", "aryloxycarbonyl", "heteroaryloxycarbonyl", "cycloalkyloxycarbonyl", "cycloheteroalkyloxycarbonyl", "aralkyoxycarbonyloxloxycarbonyl", "heteroaralkyloxycarbonyl", "(cycloalkyl)alkyloxycarbonyl", "(cycloheteroalkyl)alkyloxycarbonyl" refer to —O—C(O)R, where R is optionally substituted loweralkyl, aryl, heteroaryl, cycloalkyl, cycloheteroalkyl, aralkyl, heteroaralkyl, (cycloalkyl)alkyl, and (cycloheteroalkyl)alkyl respectively.

"Carbonylamino" refers to the group —NH—C(O)—. The terms "loweralkylcarbonylamino", "arylcarbonylamino", "heteroarylcarbonylamino", "cycloalkylcarbonylamino", "cycloheteroalkylcarbonylamino", "aralkylcarbonylamino", "heteroaralkylcarbonylamino", "(cycloalkyl)alkylcarbonylamino", and "(cycloheteroalkyl)alkylcarbonylamino" refer to —NH—C(O)R, where R is optionally substituted loweralkyl, aryl, heteroaryl, cycloalkyl, cycloheteroalkyl, aralkyl, heteroaralkyl, (cycloalkyl)alkyl, or (cycloheteroalkyl)alkyl respectively. In addition, the present invention includes N-substituted carbonylamino (—NR'C(O)R), where R' is optionally substituted loweralkyl, aryl, heteroaryl, aralkyl, or heteroaralkyl and R retains the previous definition.

"Carbonylthio" refers to the group —C(O)—S—. The terms "loweralkylcarbonylthio", "arylcarbonylthio", "heteroarylcarbonylthio", "cycloalkylcarbonylthio", "cycloheteroalkylcarbonylthio", "aralkycarbonylthio", "heteroaralkylcarbonylthio", "(cycloalkyl)alkylcarbonylthio", "(cycloheteroalkyl)alkylcarbonylthio" refer to —C(O)SR, where R is optionally substituted loweralkyl, aryl, heteroaryl, cycloalkyl, cycloheteroalkyl, aralkyl, heteroaralkyl, (cycloalkyl)alkyl, and (cycloheteroalkyl)alkyl respectively.

4.1.9 Methylene and Methine

The term "methylene" as used herein refers to an unsubstituted, monosubstituted, or disubstituted carbon atom having a formal $sp^3$ hybridization (i.e., —CRR'—, where R and R' are hydrogen or independent substituents).

The term "methine" as used herein refers to an unsubstituted or carbon atom having a formal $sp^2$-hybridization (i.e., —CR= or =CR—, where R is hydrogen a substituent).

4.2 Novel Compounds Useful for Treating Diseases
4.2.1 Definition of Novel Compounds In a first aspect, the present invention provides a compound having the structure:

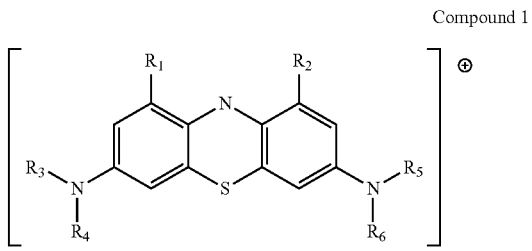

Compound 1 including the pharmaceutically acceptable salts, solvates, and hydrates thereof. $R_1$ and $R_2$ are selected independently from the group consisting of: hydrogen, halo, cyano, carbonyl, carboxyl, and optionally substituted lower alkyl, optionally substituted lower alkyloxy, and optionally substituted lower alkylcarbonyl. $R_3$-$R_6$ are selected independently from the group consisting of: optionally substituted lower alkyl and lower hydroxyalkyl, and further $R_3$ and $R_4$, and $R_5$ and $R_6$, together with the nitrogens to which they are attached respectively, may form independently an optionally substituted saturated or unsaturated five- or six-membered ring. However, none of $R_3$-$R_6$ is substituted or unsubstituted $C_{1-4}$ alkyl, substituted or unsubstituted $C_{2-4}$ alkenyl when both $R_1$ and $R_2$ are selected from the group consisting of hydrogen, $C_{1-4}$ alkyl, $C_{2-4}$ alkenyl, or halogenated $C_{1-4}$ alkyl; and none of $R_3$-$R_6$, together with the nitrogens to which they are attached respectively, forms piperazin-1-yl when both $R_1$ and $R_2$ are hydrogen.

The structural formula for Compound 1 shown above implicitly includes all equivalent resonance structures. Similarly, the illustration of any specific resonance structure herein is defined to include all equivalent resonance structures implicitly unless specifically noted otherwise. The identification of such resonance structures and their equivalents is well known to persons having ordinary skill in the art. Furthermore, although the illustrated structures herein denote cationic compounds, it will be understood that the compounds of the invention further include the illustrated cation paired with any suitable complementary anion(s). The recognition of such suitable complementary anion(s) will be apparent to those persons having ordinary skill in the art.

In some embodiments of Compound 1 at least one of $R_1$ and $R_2$ is hydrogen, and, in more specific embodiments of the foregoing, both $R_1$ and $R_2$ are hydrogen.

In other embodiments of Compound 1, at least one of $R_3$-$R_6$, together with the nitrogens to which they are attached respectively, is an optionally substituted saturated or unsaturated five- or six-membered ring; in more specific embodiments of the foregoing, the aforementioned five- or six-membered ring is saturated. Still more specific embodiments of Compound 1 just described are those in which the aforementioned saturated five- or six-membered ring is a five-membered ring. In yet more specific embodiments, the aforementioned saturated five-membered ring is pyrrolyl.

In still other embodiments of Compound 1, $R_1$ and $R_2$ are selected independently from the group consisting of: halogen, carboxyl, carbonyl, and cyano. In more specific embodiments of Compound 1, wherein $R_1$ and $R_2$ are selected independently from the group consisting of: halogen, carboxyl, carbonyl, and cyano, at least one of $R_1$ and $R_2$ is halo; and in still more specific embodiments, at least one of $R_1$ and $R_2$ is chlorine or fluorine. In yet more specific embodiments, at least one of $R_1$ and $R_2$ is fluorine, or at least one of $R_1$ and $R_2$ is chlorine. In still other embodiments of Compound 1, wherein $R_1$ and $R_2$ are selected independently from the group consisting of: halogen, carboxyl, carbonyl, and cyano, at least one of $R_1$ and $R_2$ is halo, both $R_1$ and $R_2$ is halo; and of the latter, more specific embodiments are those for which both $R_1$ and $R_2$ are chlorine or fluorine. Yet more specific embodiments of the latter are those in which both $R_1$ and $R_2$ are fluorine, those in which both $R_1$ and $R_2$ are chlorine, and those wherein one of $R_1$ and $R_2$ is chlorine and the other of $R_1$ and $R_2$ is fluorine.

Among those embodiments of Compound 1, wherein $R_1$ and $R_2$ are selected independently from the group consisting of: halogen, carboxyl, carbonyl, and cyano and both $R_1$ and $R_2$ is halo, are those further where each of $R_3$-$R_6$ is optionally substituted lower alkyl; and, more specifically, where each of $R_3$-$R_6$ is optionally substituted methyl or optionally substituted ethyl; and, still more specifically, where each of $R_3$-$R_6$ is methyl or ethyl; and, yet more specifically, where each of $R_3$-$R_6$ is methyl.

In another aspect, the invention provides the novel compound shown below:

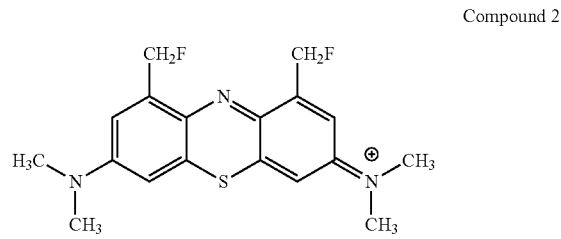

Compound 2 and its pharmaceutically acceptable salts, hydrates, and complexes.

In another aspect, the invention provides the novel compound shown below:

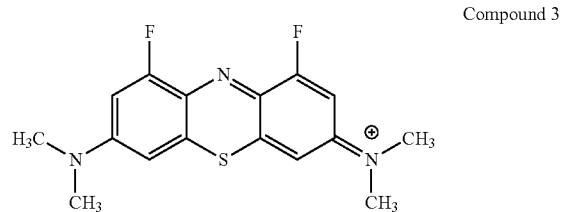

Compound 3 and its pharmaceutically acceptable salts, hydrates, and complexes.

In another aspect, the invention provides the novel compound shown below:

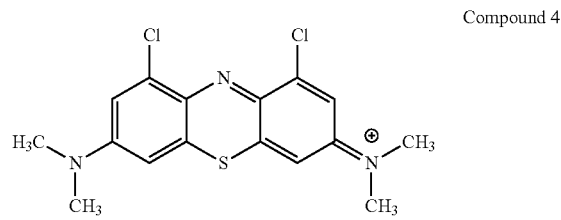

Compound 4 and its pharmaceutically acceptable salts, hydrates, and complexes.

In another aspect, the invention provides the novel compound shown below:

Compound 5 and its pharmaceutically acceptable salts, hydrates, and complexes.

In another aspect, the invention provides the novel compound shown below:

Compound 6 and its pharmaceutically acceptable salts, hydrates, and complexes.

In another aspect, the invention provides the novel compound shown below:

Compound 7 and its pharmaceutically acceptable salts, hydrates, and complexes.

4.2.2 Syntheses of Compounds of the Invention

The compounds of the invention can be made using methods and materials well known to persons having ordinary skill in the art in combination with the present disclosure. For example, embodiments of those compounds described by Compound 1 above for which $R_1$ and $R_2$ independently are hydrogen, alkyl, or halo, especially fluoro and chloro, and $R_3$-$R_6$ independently are lower alkyl, especially methyl or ethyl, or form a pyrrolidyl ring with the respective nitrogen to which they are attached, can be made by persons having ordinary skill in the art using the procedures described in published U.S. Patent Application Serial No. US 2006/0287523 A1, which is incorporated herein by reference in its entirety and for all purposes. Examples are provided in Section 4.3 below.

Compounds described by Compound 1 above for which $R_1$ and $R_2$ are both hydrogen and $R_3$-$R_6$ including the respective nitrogens to which they are attached define substituted pyrrolidyl rings can be made by persons having ordinary skill in the art using the procedures provided, e.g., in *Tetrahedron* 1997, 53(29), 10083-10092; *J. Heterocyclic. Chem.* 1993, 30, 1693; *J. Med. Chem.* 2007, 50(10), 2281-2284; and *Histochemical Journal, I* (1969), 199-20 4. Each of these references is incorporated herein by reference in its entirety and for all purposes.

Still other compounds described herein can be made by persons having ordinary skill in the art using known methods and materials.

4.3 Methods for Treating Viral Diseases

In yet another aspect, the present invention provides a method for treating an animal infected with a virus, comprising administering to such animal a therapeutically effective amount of a compound having the structure:

Compound 8 including the pharmaceutically acceptable salts, solvates, and hydrates thereof. $R_1$ and $R_2$ are selected independently from the group consisting of: hydrogen, halogen, cyano, carbonyl, carboxyl, and optionally substituted lower alkyl, optionally substituted lower alkyloxy, and optionally substituted lower alkylcarbonyl. $R_3$-$R_6$ are selected independently from the group consisting of: optionally substituted lower alkyl and lower hydroxyalkyl, and further $R_3$ and $R_4$, and $R_5$ and $R_6$, together with the nitrogens to which they are attached respectively, may form independently an optionally substituted saturated or unsaturated five- or six-membered ring.

In some embodiments, the virus is selected from the group consisting of: HCV, VEEV, RVFV, LASV, and EBOV. In specific embodiments, the virus is HCV or VEEV; in more specific embodiments, the virus is HCV, and in other more specific embodiments, the virus is VEEV. In other embodiments, the virus is LASV, RVFV or EBOV; in more specific embodiments, the is RVFV, in other more specific embodiments, the virus is EBOV, and in still other more specific embodiments, the virus is LASV.

Compounds of the invention have demonstrated activity, as measured by $EC_{99}$ (µM), across viruses of diverse families, including HCV, VEEV, RVFV, EBOV, WNV, DENY, LASV, CHK, WEEV, EEEV, and PTV, as shown in Table 1:

TABLE 1

| Compound | HCV | VEEV | RVFV | EBOV | WNV | DENV | LASV | CHK | WEEV | EEEV | PTV |
|---|---|---|---|---|---|---|---|---|---|---|---|
| Methylene Blue (MB) | 0.02-0.08 | <1 | >5 | >3.2 | <1 | 10 | | 1 | 1 | 1 | |
| Dimethyl MB | 0.2-0.5 | 0.02-0.1 | <10 | 0.025-0.1 | 0.025-0.1 | | <1 | 0.1-1 | 0.1 | <0.1 | 5 |
| Diethyl MB | | 0.1-1 | 0.1 | >3.2 | <0.05 | 0.05-1 | | 0.05 | | | |

TABLE 1-continued

| Compound | HCV | VEEV | RVFV | EBOV | WNV | DENV | LASV | CHK | WEEV | EEEV | PTV |
|---|---|---|---|---|---|---|---|---|---|---|---|
| Compound 4 | | <1 | 0.05 | <1 | | | <5 | | | | |
| Compound 3 | | <1 | >5 | 1 | | | >5 | | | | |
| Toluidine Blue | <10 | | | | | 1 | | | | | |
| Azure A | 0.1-1 | | | | | 1 | | | | | |
| Azure B | 0.1-1 | | | | | 1 | | | | | |
| Azure C | | 0.1 | | | | <1 | | | | | |
| Compound 6 | | <1 | 2.5 | <1 | | | <5 | | | | |

In addition, dimethylmethylene blue (dimethyl MB) was tested in an animal models of Ebola (EBOV) and Marburg infection as described in Section 4.4.2.1, following published methods (Bray, M., K. Davis, T. Geisbert, C. Schmaljohn, and J. Huggins. 1998. "A mouse model for evaluation of prophylaxis and therapy of Ebola hemorrhagic fever." *J. Infect. Dis.* 178:651-661, which is incorporated herein by reference in its entirety and for all purposes). The results are shown in FIGS. 1A and 1B, and FIGS. 2A and 2B respectively.

FIG. 1A shows the control group, which did not receive any compound. The control mice appear to be healthy through Day 3, but all show symptoms of stress ("ruffling") by Day 5. On Day 6 over half of the mice had died; and the other half were clearly sick with the virus. By Day 10 all mice in the control group were dead. In contrast (FIG. 1B), mice treated with the compound of the invention showed no symptoms thorough Day 5, some signs of stress between Day 6 and Day 9, and then fully recovered by Day 10. Thus, the compound of the invention provided complete prophylaxis to the study group.

FIG. 2A shows the control group, which did not receive any compound. The control mice appear to be healthy through Day 4, but all show symptoms of stress ("ruffling") by Day 5 and two mice had died. On Day 6 over all of the mice had died or were sick. By Day 7 all mice in the control group were dead. In contrast, as sown in FIG. 2B, all mice treated with the compound of the invention showed no symptoms thorough Day 3. Two mice died, and the surviving mice showed stress on Day 4. By Day 6, four mice had died and the remaining six showed stress. But by Day 9, the surviving mice had recovered. Thus, the compound of the invention provided prophylaxis to 60% of the study group.

The data shown in the Table above and the accompanying Figures demonstrate that the present invention provides compounds and methods for treating viral infections across a surprisingly broad spectrum of viral families, in sharp contrast to current chemotherapeutic methods that are usually very narrowly directed to specific viral species. Since different viral families have markedly different mechanisms for replication, the novel compounds and methods provided by the invention can be considered truly broad-spectrum anti-viral compounds and anti-viral treatments.

The novel compounds of the invention can be formulated and administered to patients using methods and materials known to persons having ordinary skill in the art. Similarly, the methods of the invention can be practiced using methods and materials known to persons having ordinary skill in the art.

4.4 Examples

The following Examples are provided to illustrate certain aspects of the present invention and to aid those of skill in the art in the art in practicing the invention. These Examples are in no way to be considered to limit the scope of the invention in any manner.

4.4.1 Syntheses of Compounds 4.4.1.1 Syntheses of Compound 3 and Compound 4

The syntheses of Compound 3 and Compound 4 are illustrated in Scheme 1.

Scheme 1

1a R = F
1b R = Cl $(MeO)_3P=O$ →

2a R = F
2b R = Cl $HCl/NaNO_2$ →

3a R = F
3b R = Cl

↓ Zn/HCl

4a R = F
4b R = Cl

← $Na_2S$ / $FeCl_3$

Compound 3 R = F
Compound 4 R = Cl

Commercially available starting materials 1a or 1b (0.1 mol) were placed under nitrogen atmosphere and combined with trimethyl phosphate (($CH_3)_2P=O$, 0.102 mol). The mixture was slowly heated to about 150° C. (over a time period of no less than 40 minutes), and the mixture was refluxed for two hours at a final temperature of about 200° C. The reaction mixture was then cooled to room temperature and slowly added to about 100 milliliters (ml) of NaOH (15 g) aq. solution. The resulting aqueous mixture was then extracted with methylene chloride ($CH_2Cl_2$) and dried over $Na_2SO_4$/NaOH. Yield 2a: 10.8 g; 2b: 12.0 g.

Next, intermediate 2a or 2b (77.7 mmol) was dissolved in about 60 ml of 6N hydrochloric acid, and the solution was slowly added to about 20 ml $NaNO_2$ aqueous solution under ice bath. The resulting mixture was stirred at room temperature for about one hour. A yellow precipitate formed, which was collected and washed with cold 2N HCl and diethyl ether to give a substantially pure desired product 3a or 3b respectively. Yield: 3a: 8.2 g; 3b: 10.0 g.

The product 3a (or 3b) (5.0 g) was then suspended in about 80 ml of 4N HCl; and enough zinc (Zn) was added to the suspension until the reaction mixture became colorless. The colorless mixture was filtered, and the filtrate was neutralized with aqueous NaOH. The aqueous solution was extracted with $CH_2Cl_2$; and the organic layer was dried with $Na_2SO_4$ and purified chromatographically with a silica gel column, by eluting with a $CH_2Cl_2$/$CH_3OH$ (100:3) solvent mixture. Yield 4a: 3.0 g; 4b 2.8 g.

4.4.1.1.1 Synthesis of Compound 3

About 2.0 g of sodium sulphide ($Na_2S.9H_2O$) was dissolved in about 8 ml of water; and about 8.1 g of ferric chloride was dissolved in 50 ml of 2N hydrochloric acid. Intermediate 4a (2.0 g) was dissolved in about 20 ml 3N HCl, and while stirring, aliquots of about 0.8 ml of the sodium sulphide solution and then about 5 ml of the ferric chloride solution were added alternately until each of the two solutions had been added. The stirring was continued for about two hours after the addition of the final aliquot, during which time a precipitate formed. The precipitate was filtered; the filter cake was dissolved in methanol; and the filtrate was extracted with $CH_2Cl_2$ (100 ml, three times). The organic layer was dried ($Na_2SO_4$) and combined with the methanol solution of the filter cake. The solution was concentrated, and the crude product was purified chromatographically over a silica gel column (several times), by eluting with $CH_2Cl_2$/$CH_3OH$ (12:1), followed by vacuum drying. Yield: 12.2 mg.

4.4.1.1.2 Synthesis of Compound 4:

About 6.4 g of sodium sulphide ($Na_2S.9H_2O$) was dissolved in about 25 ml of water, and about 8.1 g of ferric chloride was dissolved in about 160 ml of 2N hydrochloric acid. Intermediate 4b (5.0 g) was dissolved in about 65 ml 3N HCl, and while stirring, aliquots of about 1.25 ml of the sodium sulphide solution and then about 8 ml of the ferric chloride solution were added alternately until each of the two solutions had been added. The stirring was continued for about 12 hours after the addition of the final aliquot, during which time a precipitate formed. The precipitate (the crude product) was filtered, and purified chromatographically with silica gel column (several times), by eluting with $CH_2Cl_2$/$CH_3OH$ (14:1), followed by vacuum drying. Yield: 9.1 mg.

4.4.1.2 Synthesis of Compound 6

The synthesis of Compound 6 is illustrated in Scheme 2.

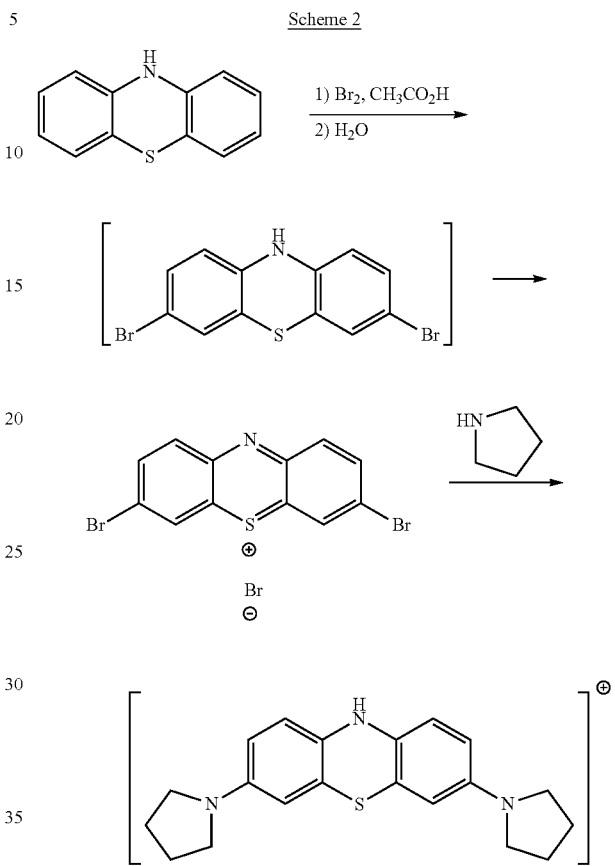

4.4.1.2.1 Synthesis of 3,7-dibromophenothiazin-5-ium bromide:

Commercially available phenothiazine (2.0 g, 10.0 mmol) was dissolved in about 120 ml of substantially oxygen-free glacial acetic acid, and a solution of bromine ($Br_2$) in acetic acid (100 ml, 10%, v/v, 195 mmol) was added to the phenothiazine solution in a single aliquot with vigorous stirring. The stirring was continued for about one minute, and then about 400 ml of water was added to the mixture whereupon a red precipitate formed. The red precipitate was filtered, washed with water and diethyl ether ($CH_3OCH_3$), and dried under vacuum. Yield: 4.4 g (crude, about 100%).

4.4.1.2.2 Synthesis of Compound 6:

To a solution of pyrrolidine (1.5 ml, 18 mmol) in about 250 ml $CHCl_3$, kept under $N_2$, about 1.0 g (2.3 mmol) of 3,7-dibromophenothiazin-5-ium bromide, prepared as just described, was added in a single aliquot with vigorous stirring. Three hours later the $CHCl_3$ was removed under vacuum, and the crude product was dissolved in about 150 ml $CH_2Cl_2$ and extracted once with about 50 ml HBr (1%, v/v) and once with about 50 ml water. The organic layer was dried over $Na_2SO_4$, concentrated, and the crude product was purified chromatographically over silica gel column (twice), by eluting first with $CH_2Cl_2$/$CH_3OH$ (20:1) and then with $CH_2Cl_2$/$CH_3OH$ (10:1). The resulting crude product was purified by re-crystallization ($CH_2Cl_2$/PE, twice) and vacuum drying. Yield: 145 mg (15%).

4.4.1.2.3 Synthesis of Compound 7

Compound 7 was made as illustrated in Scheme 3.

Scheme 3

Compound 7

4.4.2 Biological Studies
4.4.2.1 Ebola (EBOV) and Marburg Live Virus Animal Assays The test compound (methylene blue, Dimethyl MB) was dissolved in saline at 800 µg/ml and 100 µl administered twice daily by intraperitoneal injection (IP), beginning on Day 2.

The test compound (Dimethyl MB) was dissolved in saline at 160 µg/ml and 100 µg/ml administered twice daily by IP, beginning at Day 2.

Compound but no virus and Saline controls (groups 3 and 4) were administered on Day 2. All virus inoculations (Groups 1, 2 and 4) began on Day 0. Note saline control animals (Group 4) received two days of saline before virus inoculations.

1,000 pfu EBOV or Marburg virus was given to Groups 1, 2, 4, 5, and 6 by IP on Day 0.

| Group | Description | #Mice | Timing of Sacrifice (3 mice per sacrifice) |
|---|---|---|---|
| 1 (High Dose) | 1,000 pfu EBOV: 5 mg/kg/day Dimethyl MB | 16 | Day +4, Day +7, End |
| 2 (Low Dose) | 1,000 pfu EBOV: 1.0 mg/kg/day Dimethyl MB | 16 | Day +4, Day +7, End |
| 3 | 5 mg/kg/day of Dimethyl MB | 16 | Day +4, Day +7, End |
| 4 | Saline + 1000 pfu EBOV | 16 | Day +4, Day +7, End |

Mice were monitored daily for clinical signs, including ruffling, immobility. Mice were weighed each day and their weights recorded.

The results are shown for EBOV in FIGS. 1A and 1B. Mice in the control group (i.e., untreated mice) had noticeable morbidity by Day 3 and 100% mortality by Day 6. Mice treated with the compound showed morbidity starting on Day 3, but had recovered by Day 6, with a 100% survival.

The results for Marburg are shown in FIGS. 2A and 2B. Mice in the control group showed stress at Day 4, and deaths

4.4.3 Virus Yield Reduction and Standard Plaque Assays
4.4.3.1 Plaque Reduction Assay The tests described were done in triplicate for each compound shown above, at concentrations of 2.5 µM, 10 µM, and 20 µM.

Vero cells were plated on 12- or 24-well plates. When the cells were 80%-90% confluent, they were infected with 100 pfu or 50 pfu respectively of VEEV Trinidad virus at 37° C. for one hour with rocking every 15 minutes.

After infection the inoculum was removed and replaced with standard plaque assay overlay with a final concentration of 1% agar, 1×EMEM, 10% FBS, Pen/Strep, and test compound as various concentrations. These were predetermined or "serial dilutions" from high concentration. VEEV Trinidad with no test agent was included for control and comparison purposes.

The 12-well plates used 1 ml overlay for each well. The 24-well plates need 0.5 ml overlay for each well.

The plates were incubated at 37° C. and 5% $CO_2$ overnight.

At approximately 24 hpi, a secondary overlay containing final concentrations of 1% agar, 1×EMEM, 10% FBS, Pen/

Strep, and 5% neutral red was included; and the plates were incubated overnight at 37° C., 5% $CO_2$.

The plaques were counted, and the data recorded and analyzed.

The same assay was performed for EEEV, WNV, CHK, and WEEV; the respective $EC_{99}$ values for each of these viruses are shown above. Activity of DENY was determined using this protocol, wherein cells were infected with DENV at a multiplicity of infection of one (1). The cells were collected over six (6) days post-infection and analyzed as described above.

4.4.4 HCV Activity Assay
4.4.4.1.1 Replicon potency and cytotoxicity:

Huh-luc cells (stably replicating the Bartenschlager I389luc-ubi-neo/NS3-3'/ET genotype 1b replicon) were treated with serial dilutions of compound (DMSO was used as solvent) for 72 hours. Replicon copy number was measured by bioluminescence and non-linear regression was performed to calculate EC50s. Parallel plates treated with the same drug dilutions were assayed for cytotoxicity using the Promega CellTiter-Glo cell viability assay.

4.4.4.2 Potency and Cytotoxicity Against Infectious HCV:

Huh-7 cells overexpressing CD81 (called Lun-CD81) were infected for ~8 days at which point most of the cells were infected (i.e. positive for HCV core protein) and are producing virus at ~$10^3$ focus forming units (ffu)/ml.

The infected cells were seeded in 96 well and 24 well plates at a density of $5 \times 10^3$/well and $2.5 \times 10^4$/well, respectively. The next day, cells were washed 3× with PBS and compound dilutions (in complete DMEM) were added to each well. Cells were then incubated for 3 days at 37° C.

At the end of three days, infection and virus production were analyzed the following ways:
 a. RNA replication ($EC_{50}$)—96 well plate was used for $EC_{50}$ analysis using a novel NS3 protease substrate assay.
 b. Virus production ($EC_{50}$)—Supernatants were removed from the 24 well plate and an end point limit dilution assay was performed in which naive cells were infected for an additional three days to quantitate the amount of infectious virus in the supernatant. Cells were then fixed with 4% paraformaldehyde and indirect immunofluorescence was performed using an anti-HCV core antibody. HCV-positive foci were counted at each compound dilution to calculate the EC50 value.
 c. Cytotoxicity ($EC_{50}$)—96 well plate was used for $EC_{50}$ analysis using the Promega CellTiter-Glo assay.

4.4.5 Standard Plaque Assay for RVFV and LASV

About 540 μl of media (complete EMEM) was aliquoted into 6 rows of a titer box. Sample dilutions were made by adding about 60 μl of each sample was added to the first well in each row. All samples were added first, and then diluted to 1:10 for six dilutions total down the plate (60 μl into 540 μl, with thorough mixing before each transfer by pipetting up and down six times). A positive control was included.

The media from Vero 6-well plates was emptied into a dispo/kill pan with microchem. The plate was 200 μl/well in duplicate (top and bottom). Started with –6 dilution and used the same tip until –1 dilution according the following pattern:

| -1 | -2 | -3 |
|----|----|----|
| -1 | -2 | -3 |

-continued

| -4 | -5 | -6 |
|----|----|----|
| -4 | -5 | -6 |

The plates were rocked well after putting on the samples to disperse virus throughout the wells.

Samples were incubated for about one (1) hour at 37° C., making sure to rock plates every 15 minutes, so the middle plate di not dry out.

The plates were warmed 2×EBME+10% FBS+1% gent to 37° C. in a water bath.

A 1% agarose (1 g agarose in 100 ml di$H_2O$) was prepared and heated by microwave until agar was dissolved. The remaining solution was cooled to 45° C. in the water bath during the incubation.

The plates were removed from incubator and equal parts of 2×EBME and 1% agarose were mixed immediately before overlaying (to avoid clumping and solidifying. About 2 ml of overlay media (2×EBME+suppl/1% agarose) per well was added, about 12 ml overlay/plate.

On day three, another overlay was done with 2 ml of overlay media+4% neutral red solution (4 ml/100 ml of overlay).

The number of plaques at each dilution was read on following day.

5 Conclusion

Those of persons having ordinary skill in the art will appreciate from the foregoing that the present invention provide novel compounds and methods that are important additions to existing anti-viral therapies and provide truly broad-spectrum anti-viral activity. The latter properties are vital to providing chemotherapeutics capable of addressing the growing threats from existing viruses, newly emergent viruses, and weaponized viruses. Although various specific embodiments and examples have been described herein, those having ordinary skill in the art will understand that many different implementations of the invention can be achieved without departing from the spirit or scope of this disclosure.

What is claimed:
1. A compound having the structure:

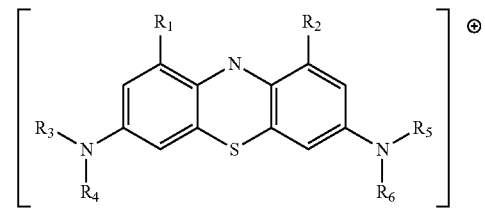

and its pharmaceutically acceptable salts, hydrates, and coordination compounds, wherein:
$R_1$ and $R_2$ are selected independently from the group consisting of: hydrogen, halo, cyano, carboxyl, and optionally substituted lower alkyl, optionally substituted lower alkyloxy, and optionally substituted lower alkylcarbonyl; and
each of $R_3$ and $R_4$, and $R_5$ and $R_6$, together with the nitrogens to which they are attached respectively, independently is optionally substituted pyrrolidin 1-yl.

2. The compound of claim 1, wherein at least one of $R^3$ and $R^4$, together with the nitrogen atom to which they are attached, and $R^5$ and $R^6$, together with the nitrogen atom to which they are attached, is pyrrolidin-1-yl.

3. The compound of claim 2, wherein both of $R^3$ and $R^4$, together with the nitrogen atom to which they are attached, and $R^5$ and $R^6$, together with the nitrogen atom to which they are attached, are pyrrolidin 1-yl.

4. The compounds of claim 3, having the structure:

[structure]

5. The compound of claim 1, wherein $R_1$ and $R_2$ are selected independently from the group consisting of: halogen, carboxyl, carbonyl, and cyano.

6. The compound of claim 5, wherein at least one of $R_1$ and $R_2$ is halo.

7. The compound of claim 6, wherein said at least one of $R_1$ and $R_2$ is chlorine or fluorine.

8. The compound of claim 7, wherein said at least one of $R_1$ and $R_2$ is fluorine.

9. The compound of claim 7, wherein said at least one of $R_1$ and $R_2$ is chlorine.

10. The compound of claim 6, wherein both $R_1$ and $R_2$ is halo.

11. The compound of claim 10, wherein both $R_1$ and $R_2$ are chlorine or fluorine.

12. The compound of claim 11, wherein both $R_1$ and $R_2$ are fluorine.

13. The compound of claim 11, wherein both $R_1$ and $R_2$ are chlorine.

14. The compound of claim 11, wherein one of $R_1$ and $R_2$ is chlorine and the other of $R_1$ and $R_2$ is fluorine.

15. The compound of claim 11, wherein each of $R_3$-$R_6$ is optionally substituted lower alkyl.

16. The compound of claim 15, wherein each of $R_3$-$R_6$ is optionally substituted methyl or optionally substituted ethyl.

17. The compound of claim 16, wherein each of $R_3$-$R_6$ is methyl or ethyl.

18. The compound of claim 17 wherein each of $R_3$-$R_6$ is methyl.

19. A method for treating an animal infected with a virus, comprising administering to such animal a therapeutically effective amount of a compound having the structure:

[structure]

and its pharmaceutically acceptable salts, hydrates, and coordination compounds, wherein:

$R_1$ and $R_2$ are selected independently from the group consisting of: hydrogen, halo, cyano, carbonyl, carboxyl, and optionally substituted lower alkyl, optionally substituted lower alkyloxy, and optionally substituted lower alkylcarbonyl; and each of $R_3$ and $R_4$, and $R_5$ and $R_6$, together with the nitrogens to which they are attached respectively, independently is optionally substituted pyrrolidin-1-yl.

20. The method of claim 19, wherein said virus is selected from the group consisting of: HCV, VEEV, RVFV, LASV, and EBOV.

21. The method of claim 20, wherein said virus is HCV or VEEV.

22. The method of claim 21, wherein said virus is HCV.

23. The method of claim 21, wherein said virus is VEEV.

24. The method of claim 20, wherein said virus is LASV, RVFV or EBOV.

25. The method of claim 24, wherein said virus is RVFV.

26. The method of claim 24, wherein said virus is EBOV.

27. The method of claim 24, wherein said virus is LASV.

* * * * *